United States Patent
Demers et al.

(10) Patent No.: US 6,755,788 B2
(45) Date of Patent: Jun. 29, 2004

(54) IMAGE ORIENTATION DISPLAY FOR A THREE DIMENSIONAL ULTRASONIC IMAGING SYSTEM

(75) Inventors: Douglas Armand Demers, Haverhill, MA (US); Mckee Dunn Poland, Andover, MA (US)

(73) Assignee: Koninklijke Philips Electronics N. V., Eindhoven (NL)

( * ) Notice: Subject to any disclaimer, the term of this patent is extended or adjusted under 35 U.S.C. 154(b) by 0 days.

(21) Appl. No.: 10/437,834

(22) Filed: May 12, 2003

(65) Prior Publication Data

US 2003/0195421 A1 Oct. 16, 2003

Related U.S. Application Data

(63) Continuation-in-part of application No. 10/231,704, filed on Aug. 29, 2002, which is a continuation-in-part of application No. 09/641,306, filed on Aug. 17, 2000, now Pat. No. 6,443,896.

(51) Int. Cl.[7] .................................. A61B 8/02
(52) U.S. Cl. ....................................... 600/447
(58) Field of Search ................... 600/447, 443, 600/459, 445, 456; 345/419; 73/606, 625; 128/916

(56) References Cited

U.S. PATENT DOCUMENTS

| 5,050,610 A | | 9/1991 | Oaks et al. |
|---|---|---|---|
| 5,207,225 A | * | 5/1993 | Oaks et al. .................. 600/443 |
| 5,353,354 A | | 10/1994 | Keller et al. |
| 5,454,371 A | * | 10/1995 | Fenster et al. .............. 600/443 |
| 5,546,807 A | * | 8/1996 | Oxaal et al. .................. 73/606 |
| 5,608,849 A | * | 3/1997 | King, Jr. ..................... 345/419 |
| 6,099,474 A | * | 8/2000 | Solek .......................... 600/459 |
| 6,241,675 B1 | * | 6/2001 | Smith et al. ................. 600/443 |
| 6,245,017 B1 | * | 6/2001 | Hashimoto et al. ......... 600/447 |
| 6,276,211 B1 | | 8/2001 | Smith |
| 6,413,219 B1 | * | 7/2002 | Avila et al. .................. 600/443 |
| 6,443,896 B1 | * | 9/2002 | Detmer ....................... 600/445 |
| 6,447,454 B1 | | 9/2002 | Chenal et al. |

* cited by examiner

*Primary Examiner*—Mary Beth Jones
*Assistant Examiner*—Ruby Jain
(74) *Attorney, Agent, or Firm*—W. Brinton Yorks, Jr.

(57) ABSTRACT

A plurality of planes are scanned in real time to provide a display of images in the scanned planes in real time. The displayed images are accompanied by an orientation icon which depicts the relative inclination of the displayed planes. The icon includes a perspective view of the outline of one of the images as seen from the scanning transducer, with the aspect ratio of the outline varying to provide a visual depiction of the instantaneous inclination of the image planes. The icon may also include a numerical indication of the relative inclination and an indication of the left-right orientation of the images relative to the scanning transducer.

16 Claims, 7 Drawing Sheets

IMAGE ORIENTATION DISPLAY FOR A THREE DIMENSIONAL ULTRASONIC IMAGING SYSTEM

This is a continuation in part application of U.S. patent application Ser. No. 10/231,704, filed Aug. 29, 2002, which is a continuation in part application of U.S. patent application Ser. No. 09/641,306, filed Aug. 17, 2000 and now U.S. Pat. No. 6,443,896.

This invention relates generally to ultrasonic imaging and, more particularly, to creating multiple planar ultrasonic images of a volumetric region of the body in real-time.

A major advantage of three-dimensional ultrasonic imaging is the ability it provides to obtain unique image planes through the volume of an object such as a human body, image planes not available through conventional two-dimensional scanning. For example, through three-dimensional imaging techniques one can look simultaneously at several different cut planes of a region of tissue to thereby observe features from different angles or views. Alternatively, it may be desirable in certain instances to view an image plane at a constant depth below the object surface such as the skin. Such an image plane cannot be obtained with normal two-dimensional scanning because of the orientation of the ultrasonic probe relative to the object.

With the ability to acquire multiple image planes of a volumetric region comes the need to define the planes to be imaged, their relationship to each other in space, and the best way to display the images. In the past, a common display technique has been to display three ultrasound images of a volumetric region which are of mutually orthogonal planes. Each image has two orthogonal cross-hairs displayed over it, depicting the positions of the other two orthogonal image planes. As the cross-hairs are dragged to different positions, a new parallel image plane in that dimension is selected and displayed. These images have generally been static (non-real time) images which were reconstructed from a previously acquired volumetric echo data set. This display technique enables the clinician to survey and define tissue structures in a volumetric region by their appearances in intersecting image planes.

Such a display is useful for static image data of a volumetric region, which can readily be appropriately readdressed for display of different image planes as the selection cross-hairs are moved. The display technique does not lend itself to real-time imaging, as the complexity of control and display would be increased significantly for real-time imaging. Furthermore, such a real-time display can present too much information for the clinician to analyze in a methodical or organized manner. Hence there is a need for effective display and control of multiple real-time planar images of a volumetric region.

In accordance with the principles of the present invention, method and apparatus are described for creating and displaying multiple planar images of a volumetric region of the body. In one aspect of the invention, two real-time image planes are acquired and displayed in what is referred to herein as a "biplane" display format. The two planes of the biplane display can be controlled in two control modes, one in which an image plane is tilted relative to another image plane, and another in which one image plane is rotated relative to the other. As an image plane is tilted, the appearance of the icon changes correspondingly. In an illustrated embodiment the icon represents the outline of a sector image, the aspect ratio of which changes as the tilt control is manipulated.

Figure 1:
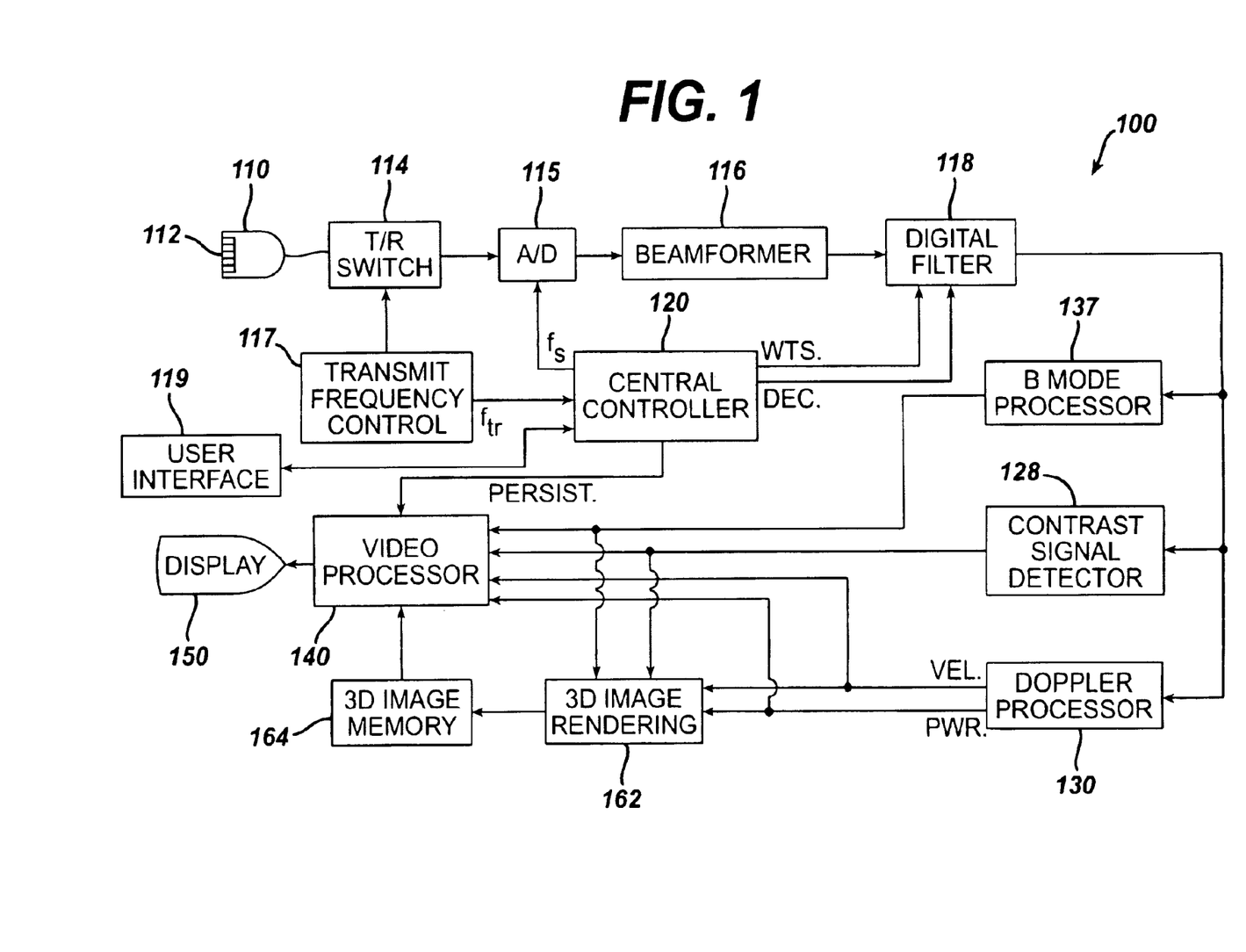
FIG. 1 is a block diagram of an ultrasonic diagnostic imaging system constructed in accordance with the principles of the present invention.

FIG. 1 is a block diagram of an ultrasonic diagnostic imaging system 100 with which methods and apparatus in accordance with the invention can be used. It should be understood that the invention is not limited to use with this imaging system but is shown implemented therein only as an example. In the imaging system 100, a central controller 120 commands a transmit frequency control 117 to transmit a desired transmit frequency band. The parameters of the transmit frequency band, $f_{tr}$, are coupled to the transmit frequency control 117, which causes a transducer 112 of an ultrasonic probe 110 to transmit ultrasonic waves in the selected frequency band. It will be understood, of course, that any ultrasonic frequency or group of frequencies, known as a frequency signature, may be used, with due consideration of the desired depth of penetration and the sensitivity of the transducer and ultrasonic system.

The transducer 112 of the probe 110 comprises an array of discrete elements that transmit ultrasonic energy in the form of a beam, and receive echo signals returned in response to this transmission. The beam can be steered to scan different parts of an object by mechanically moving the probe or, preferably, by electronically adjusting the timing of the transmission for the various array elements. In image system 100, this steering is controlled by central controller 120. The controller 120, in turn, responds to commands from a user entered via a user interface 119 that includes an interface program and a pointing device (such as a mouse, trackball, stylus, tablet, touch screen or other pointing device), keyboard, or other input device for conveying instructions to the central controller. Alternatively, the controller may be programmed to steer the beam automatically in a predetermined, default manner. The received signals are coupled through a transmit/receive (T/R) switch 114 and digitized by an analog-to-digital converter 115. The sampling frequency $f_s$ of the A/D converter is controlled by the central controller 120. The desired sampling rate dictated by sampling theory is at least twice the highest frequency $f_c$ of the received echoes. Sampling rates higher than the minimum requirement can also be used. The signal samples are delayed and summed by a beam former 116 to form coherent echo signals. The coherent echo signals are then filtered by a digital filter 118 to a desired passband. The digital filter 118 can also shift the frequency band to a lower or baseband frequency range. The characteristics of the digital filter are controlled by the central controller 120, which provides the filter with multiplier weights and decimation control. Preferably the arrangement is controlled to operate as a finite impulse response (FIR) filter, and performs both filtering and decimation. A wide range of filter characteristics is possible through programming of the weighting and decimation rates of the filter, under control of the central controller 120. The use of a digital filter allows the advantage of flexibility in providing different filter characteristics. A digital filter can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence, simply by changing the filter coefficients during signal processing.

From the digital filter 118, the filtered echo signals are detected and processed by a B mode processor 137, a contrast signal detector 128, or a Doppler processor 130. The B mode processor performs functions that include, but are not limited to, frequency compounding, spatial compounding, harmonic image formation, and other typical B mode functions that are well known in the art. The Doppler processor applies conventional Doppler processing to the echo signals to produce velocity and power Doppler signals. The outputs of the processors 137 and 130 and contrast signal detector 128 are coupled to a video processor 140 for display as a two-dimensional ultrasonic image on the display 150. The central controller 120 keeps track of the sequence of the incoming signals, and so enables the video processor 140 to place the current data in the forming image. As signals are received by the video processor 140, the data is fed to the display, producing rasterized images. The outputs of the two processors and contrast signal detector are also coupled to a three-dimensional image rendering processor 162 for the rendering of three-dimensional images, which are stored in a 3D image memory 164 and provided from there to the video processor 140. Three-dimensional rendering may be performed in a conventional manner. With this arrangement, an operator can select among the outputs of the contrast signal detector 128 and the processors 137 and 130 for two- or three-dimensional display of an ultrasonic image.

The system of FIG. 1, through the operation and control of the probe 110, transducer 112, the video processor 140, and/or the image rendering processor 162, provides the ability to create multiple real-time planar images of a volumetric region of an object such as a human body, while the body is being scanned. These planar images, when taken as slices through a body, have known geometric relationships to each other, enabling a diagnostician to view body features from different orientations. The clinician may wish to adjust the relative angles of the slices to visualize spatial relationships of tissue features. Through user interface 119, an operator can adjust the orientation of the slices displayed to align them with the features of interest in the image. Real-time performance is achieved by generating only certain ultrasonic beams needed to construct the desired planar images, rather than the much greater number of beams that would have to be transmitted to scan the entire volumetric region.

Figure 2A:
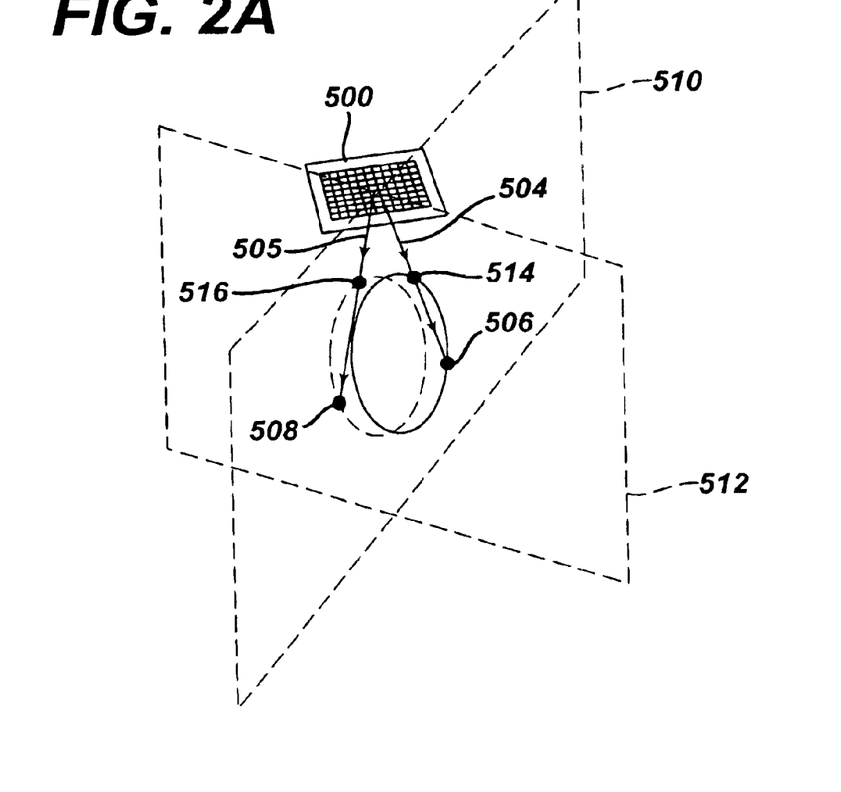
FIGS. 2A and 2B show a real time display of planar images created by use of a two dimensional array transducer with the system of FIG. 1.
Figure 2B:
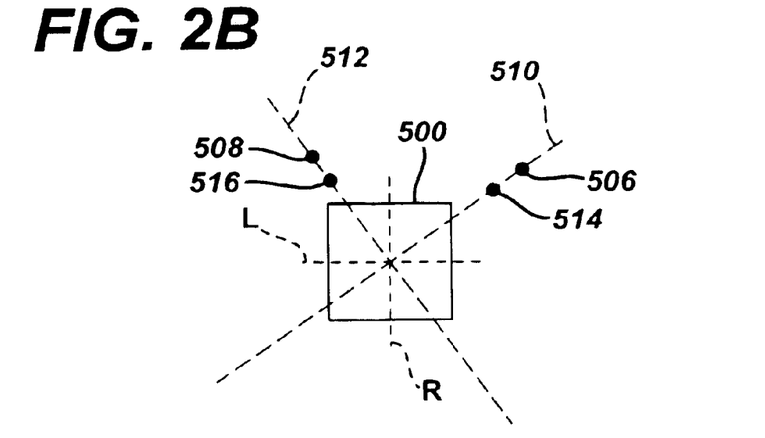

FIGS. 2A and 2B show an embodiment of a transducer 500 that can be used to obtain data from a set of planes 510 and 512. This embodiment generates beams such as beam 504 that lies in plane 510, intersecting points 514 and 506; also beam 505 that lies on plane 512, intersecting points 516 and 508. The rays emanating from two-dimensional array transducer 500 can be electronically steered in three dimensions, thus avoiding the need to mechanically sweep the transducer across the volumetric region of interest. In similar fashion, data is received from the lines of interest in the respective planes using well-known beam steering and focusing and/or gating techniques applicable to a two-dimensional array transducer.

The above scanning method for generating two planar images is preferred because of its speed, but is not exclusive. Variations are possible. If desired, additional beams can be generated which lie in and thereby define additional planes, or intersect additional surfaces. Each additional beam, of course, takes additional time to generate and therefore affects the sweep rate. The desired number of planes and their orientation is conveyed to central controller 120 through user interface 119. In addition, the transducer 112 can be controlled to emit beams directed toward more than one point in each plane. Alternatively, the transducer can be controlled to emit beams at fewer than all surfaces at each sampling position, as long as the beams lie in at least two planes, or intersect at least two non-planar surfaces, or lie in at least one plane and intersect at least one non-planar surface, per sweep. These and other obvious variations can produce multiple planar images in real-time, but at different rates and with different resolutions, depending on the variation chosen. Furthermore, any two-dimensional ultrasonic imaging technique, for example, B mode, contrast signal detection, harmonic imaging, or Doppler imaging, can be applied equally well with this data acquisition scheme.

The data acquired from the two planes 510 and 512 are used by one or more of the processors 137, 130, or the contrast signal detector 128 to construct the corresponding planar images. The planar images are preferably created at a scanning rate to provide real-time imaging. The planar images can be simultaneously displayed side-by-side by the video processor 140, or in a three dimensional perspective view on the display 150 as the volumetric region is continuously scanned, or viewed later.

Figure 3:
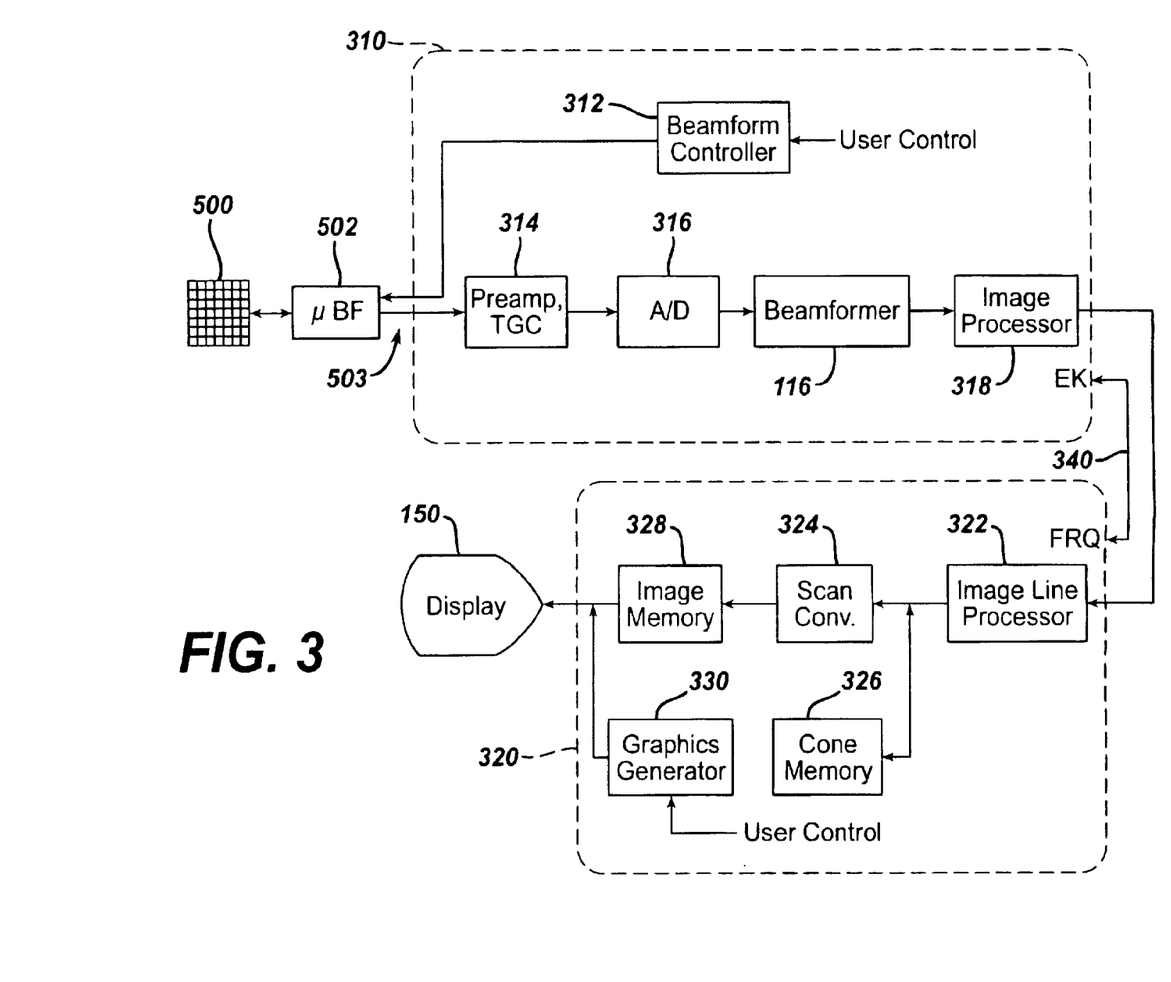
FIG. 3 illustrates in block diagram form a second embodiment of an ultrasonic diagnostic imaging system constructed in accordance with the principles of the present invention.

FIG. 3 illustrates another embodiment of an ultrasound system constructed in accordance with the principles of the present invention. In this embodiment the probe 110 includes a two dimensional array transducer 500 and a micro-beamformer 502, also known as a subarray beamformer. The micro-beamformer contains circuitry which control the signals applied to groups of elements ("patches" or "subapertures") of the array transducer 500 and does some processing of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control and provides control signals to the microbeamformer 502 instructing the probe as to the timing, frequency, direction and focusing of transmit beams. The beamform controller also controls the beamforming of received echo signals by its coupling to the analog-to-digital (A/D) converters 316 and the beamformer 116. Echo signals received by the probe are amplified by preamplifier and TGC (time gain control) circuitry 314 in the scanner, then digitized by the A/D converters 316. The digitized echo signals are then formed into beams by a beamformer 116. The echo signals are then processed by an image processor 318 which performs digital filtering, B mode detection, and Doppler processing as described above, and can also perform other signal processing such as harmonic separation, speckle reduction through frequency compounding, and other desired image processing.

The echo signals produced by the scanner 310 are coupled to the digital display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-theta conversion as is known in the art. The image is then stored in an image memory 328 from which it can be displayed on the display 150. The image in memory is also overlayed with graphics to be displayed with the image, which are generated by a graphics generator 330 which is responsive to a user control. Individual images or image sequences can be stored in a cine memory 326 during capture of image loops.

For real-time volumetric imaging the display subsystem 320 also includes the 3D image rendering processor 162 which receives image lines from the image line processor 322 for the rendering of a real-time three dimensional image which is displayed on the display 150.

In accordance with the principles of the present invention, two images, referred to herein as biplane images, are acquired by the probe in real time and displayed in a simultaneous display format. Since the 2D array 500 has the ability to steer transmitted and received beams in any direction and at any inclination in front of the array, the planes of the biplane image can have any orientation with respect to the array and to each other, as shown by the orientation of image planes 510, 512 to the array 500 in FIGS. 2A and 2B. In an embodiment illustrated below the two image planes intersect the center of the array 500 and are orthogonal to the sides of the array as shown by planes L and R in FIG. 2B, in which the planes are viewed "edge-on" from the array transducer. In the examples given below the image format is the sector image format, with the image lines emanating from a near-field apex. However, linear or steered linear scan formats can also be employed.

The biplane images in the two image planes are acquired by transmitting and receiving beams of each image as exemplified by the acquisition of beams 504 and 505 in the respective image planes of FIG. 2A. Various acquisition sequences can be performed. All of the scanlines of one image can be acquired, followed by acquisition of all of the scanlines of the other image. Alternatively, acquisition of the lines of the two images can be time interleaved. For instance, line 1 of one image can be acquired, followed by the acquisition of line 1 of the other image. This would be followed by the acquisition of line 2 of each image, then line 3 of each image, and so forth. This may be advantageous when doing Doppler image of low flow velocities, as the interval between interrogations of an ensemble of lines can be lengthened. It also advantageously results in the lines at the intersection of the two planes being acquired in succession, which prevents rapidly moving tissue at the image intersection from appearing different in the two images. The lines can be acquired in their spatial progression in the image, or sequentially from separated portions of the image. For instance, the four edge lines can be acquired first, followed by the four central lines around the intersection of the planes, then progressing alternately toward and away from the intersection.

When all of the lines of both images have been received by the scanner 310 and forwarded to the display subsystem 320, the scanner sends an "EK" signal over control lines 340 to the display subsystem, telling the display subsystem that all of the lines for the current display frame have been sent for display. The display subsystem then processes the image lines for display. For the biplane format described below, one image is processed, formatted and mapped for display on one side of the display screen and the other image is processed, formatted and mapped for display on the other side of the display screen. After the images have been processed the display subsystem returns an "FRQ" control signal to the scanner, informing the scanner that the display subsystem is requesting another image frame for processing. The complete screen display of two side-by-side images is overlaid with the graphics for the images and displayed on the display 150. The display subsystem then awaits the completion of another scanning of the two images as indicated by the concluding receipt of another EK signal, at which time the processing and display of another real time display frame proceeds again.

It is also possible to use a communication architecture in which each image is concluded with an EK signal and the transmission and receipt of both biplane images, each concluded by an EK signal and responded to by an FRQ signal, is done before a two-image display frame is produced by the display subsystem.

Figure 4:
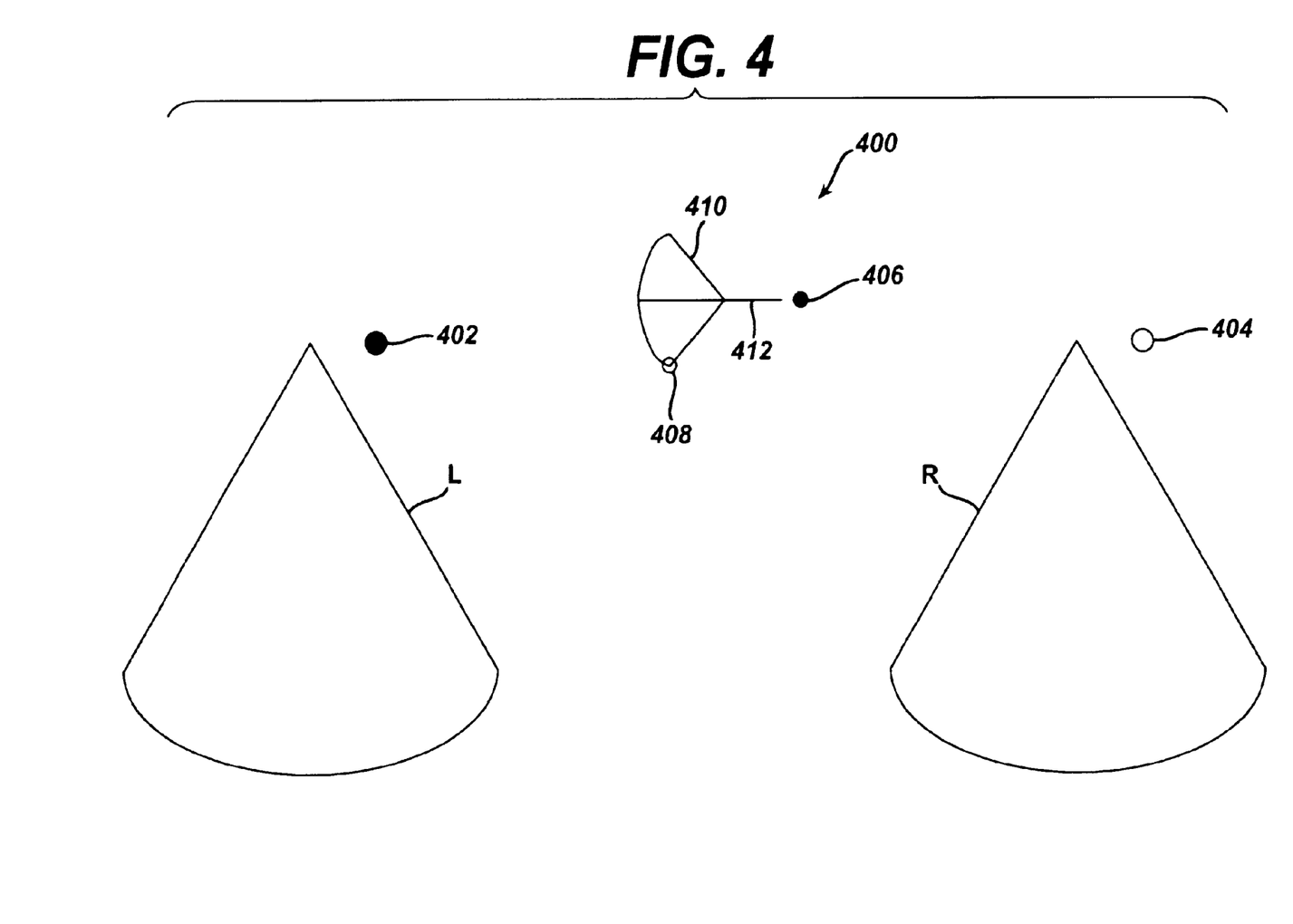
FIG. 4 illustrates a biplane display with a plane orientation icon illustrating the tilt angle of one image plane to the other.

The images in the embodiment of FIG. 4 are displayed side-by-side as illustrated graphically by images L and R in FIG. 4. In operation the image plane orientations can be selected by two selection modes, "rotate" or "tilt." In a constructed embodiment, the orientation of one image, the left image L in FIG. 4, is fixed in relation to the transducer array. The L image is always in a plane which is orthogonal to the plane of the array, extending through the center of the array as shown in FIG. 2B. The plane of the right image R can be rotated or tilted by user control relative to the plane of image L. In the rotate mode, the two images share a common center line during sector imaging, and the plane of the right image R can be rotated by manipulation of a user control such as a trackball or knob. The right image can be rotated from being co-planar with the left reference image to a 90° orientation and through to co-planar again. A full 360° of rotation is possible either by manipulation of the user control or by left-to-right inversion of the image. In the tilt mode the center of the right image R intersects the reference image, but can be tilted to intersect different lines of the reference image as if the sector is swinging from the common apex of the two images.

In a preferred embodiment the probe 110 has a marker on it which identifies a given side of the image. Generally this marker is a physical protrusion or color on one side of the probe case. Clinicians use this marker to relate the orientation of the probe to the orientation of the image on the display. It is customary to display the marker on the display screen as shown by dot 402 in FIG. 4. The clinician will generally always hold the probe with the probe marker in the same position so that the image always is shown with an orientation which the clinician prefers. In accordance with a further aspect of the present invention, the second image R is also shown with an orientation marker 404. In the rotate mode the two images can both be imaging the same plane when scanning is initiated, in which case the markers are spatially aligned. The clinician can then rotate or tilt the right image plane from the common starting orientation. In a constructed embodiment the initial condition of the two biplane images is that the two are aligned untilted along a common center line and rotated 90° with respect to each other.

In accordance with a further aspect of the present invention, an icon 400 is displayed on the biplane display to graphically indicate the relative orientation of the two image planes. The icon 400 in FIG. 4 represents a view of the image planes of the R and L images from the transducer array. At the start of the tilt mode the two images may have a nominal orientation, such as being orthogonal to each other and intersecting at their center lines. When the R and L image planes are in that orientation the icon 400 would appear as a cross ("+"), representing the view from above of two sectors, as if the viewer were looking at the sloping sides of the sectors from above. As one of the image planes is tilted in a given direction, the outline of the sector comes into view dynamically as the angle of tilt is increased. The icon 400 represents the orientation when one of the image planes, the right one R in this example, has been tilted 45° to the left, and the sector-shaped part 410 of the icon has come into view as a sector shape. The part 410 of the icon 400 will not have the identical shape as the outline of the image R it represents because the icon still displays the sector as if viewed from above, from the plane of the array transducer. Thus, the sector part 410 is given an aspect ratio to depict it as being viewed from above. As the image plane is increasingly tilted the aspect ratio of the sector part 410 continually changes in correspondence to how it would appear from the viewpoint, in this example, the transducer array. The left image L does not change its orientation relative to the transducer array in this example and constantly remains as the line part 412 of the icon 400, continually representing the edge-on view of the L sector image from above.

The dot 406 of the icon 400 corresponds to the dot 402 of the left reference image L and indicates that the plane of the reference image is in a horizontal orientation in this example with the marker at the right of the image. The open circle 408 of the icon 400 corresponding to dot 404) at the right side of the tilted R image.

In this example the R image plane has a tilt range of ±45° relative to a nominal 0° orientation where the center lines of the two images intersect. When each image is a ninety degree sector, this means that when the R image is tilted a full 45°, its center line is aligned with the edge 414 of the L image.

Figure 5A:
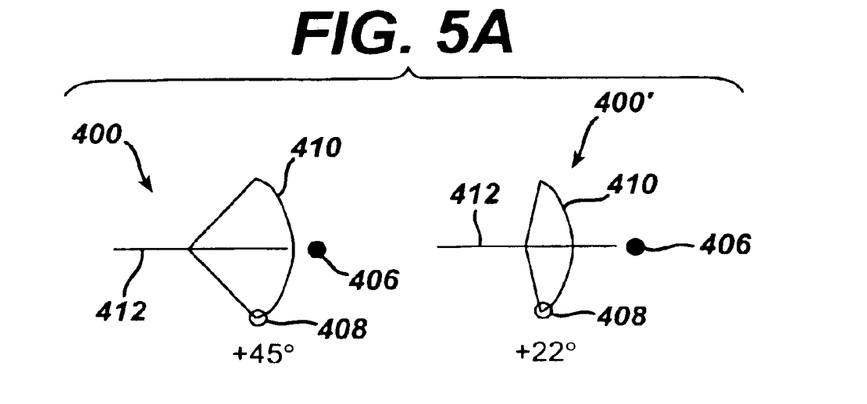
FIGS. 5A–5C illustrate the plane orientation icon of FIG. 4 for different image plane orientations.
Figure 5B:
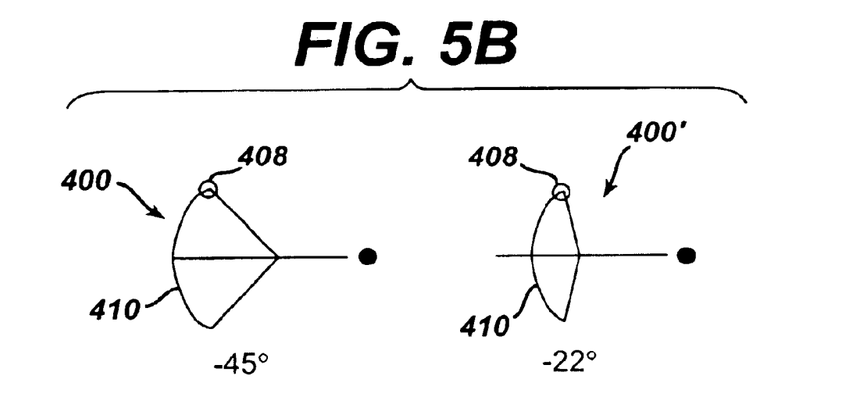
Figure 5C:
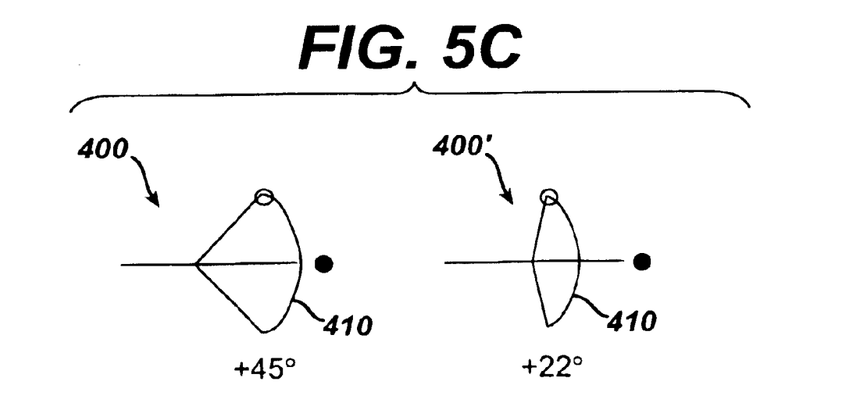

FIGS. 5A–5C illustrate how the icon 400 changes as the right image is tilted to various orientations and the images are inverted from left to right. When the right image R is tilted 45° from the center line of the L reference image, the icon 400 will appear as shown in FIG. 5A, in which the line 412 and dot 406 represent the L image and its orientation with respect to the probe and the sector part 410 shows that the R plane has tilted to the right. In this embodiment the icon 400 includes a numerical indication of the tilt angle of the R image plane, which is +45° in this example. The "+" or "−" direction may be set by the user depending upon the directional convention desired by the user. To the right of the icon 400 is another illustrated icon 400' which shows the appearance of the icon when the R image is tilted +22° to the right. As is evident, the aspect ratio of the sector part 410 in this icon 400' is different from that of the icon 400 when the R plane was tilted at 45°. The dynamic change of the aspect ratio of the sector part 410 as the tilt angle is changed gives an intuitive sense of the relative planar orientation to the user.

In a constructed embodiment the user interface of the ultrasound system includes a "right image invert" control. When this control is actuated, the right image R immediately inverts laterally by 180°, and the icon will correspondingly switch from that shown in FIG. 5A to that shown in FIG. 5C. This image inversion is apparent from the switch of the open circle 408 of the icon from the bottom of the part 410 of the icon to the top. In FIG. 5B the R image plane tilt has been changed to −45° and −22° as is evident from the appearance of the sector part 410 of the icons 400, 400' in FIG. 5B. When the right image plane is tilted to orientations of +45° and +22° the orientation icon will have the appearances shown in FIG. 5C.

A constructed embodiment of the present invention which has a "right image invert" control will also generally have a "left image invert" control so that the user may laterally invert the left image L.

An advantage of the common display of the biplane images and the icon 400 is that when the images on the display screen are saved, the icon is also saved without further effort by the sonographer. During later review of the images by a clinician the orientation of the two image planes is shown on the display or in a print of the screen. The screen display can be saved either in hard copy or electronically, and can be retrieved and referred to later to enable the patient to be scanned again with the same biplane image orientation.

Figures 6, 7:
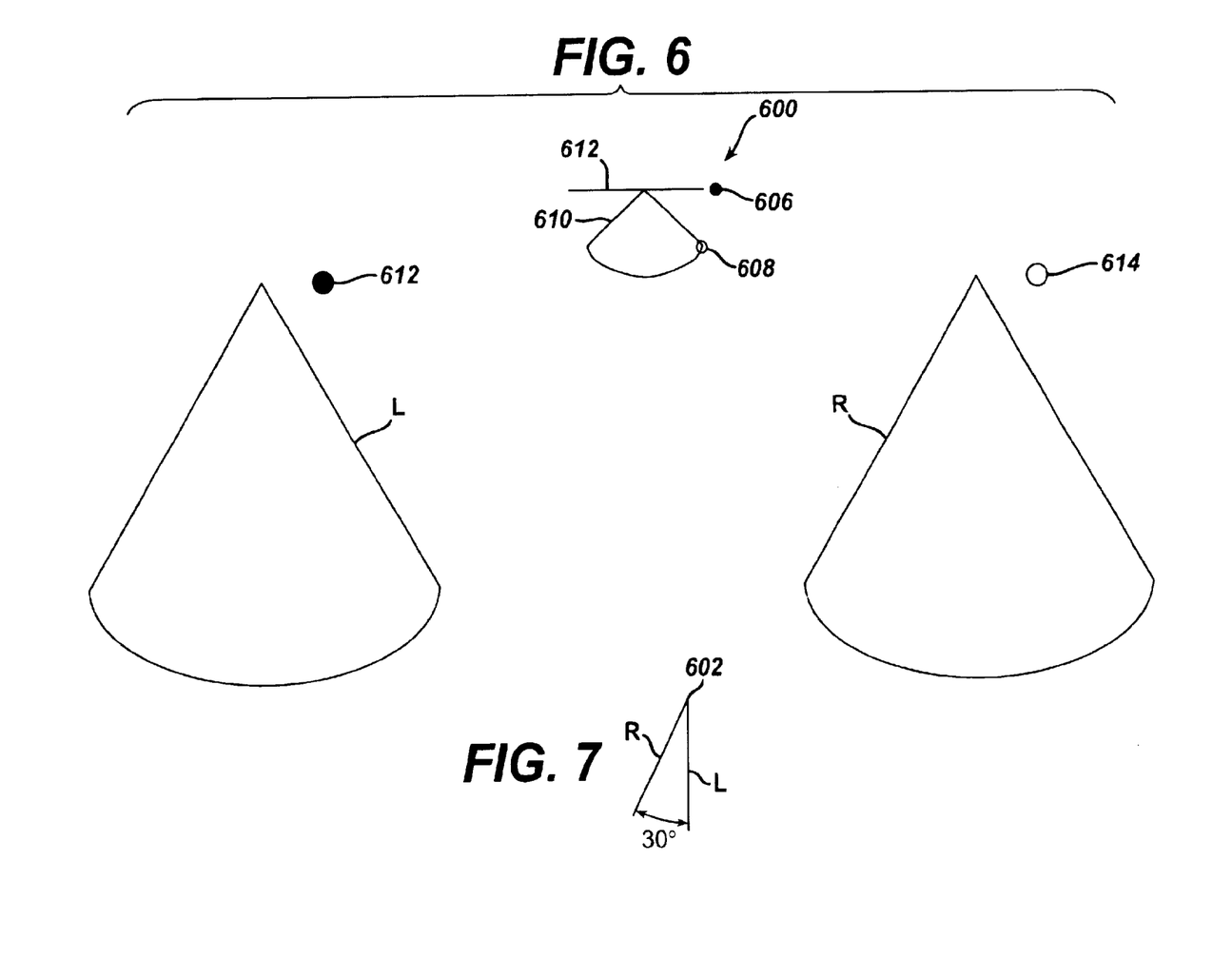
FIG. 6 illustrates a biplane display and image orientation icon for operation in the "elevation tilt" mode.
FIG. 7 is an edge-on illustration of the two image planes of FIG. 6.

FIG. 6 illustrates another biplane display with an image orientation icon 600 for a tilt control which tilts the two image planes relative to a nominal parallel orientation, that is, the two image planes are identical. This mode of display is referred to herein as the "elevation tilt" mode. The image planes are tilted relative to each other by changing the angle of inclination of at least one of the planes. The images move through selectable positions in which the planes are normal to an arc of variation extending through the planes. Conceptually, it is as if the two L and R sector images are hinged at the apexes and can swing in an arc where the two planes are always separated by the same distance at any given common depth. This motion is illustrated by the edge-on view of the L and R planes in FIG. 7, where the L and R planes have a common apex 602, image L is normal to the plane of the 2D transducer array (not shown), and image R has been tilted to be at a 30° angle from the plane of image L. The orientation icon 600 again views both image planes as if being viewed from the perspective of the transducer array, and again the reference image L is seen as a straight line 612 because it is being viewed edge-on from the top. The image plane R is depicted by sector-shaped icon part 610 which moves above and below the line 612 of the L image as the R image plane is tilted to either side of the L image plane. In this example the L image plane is fixed in orientation so as to always be at 90° to the plane of the transducer array. The two parts of the icon 600 also shown the left-right dots indicating orientation with a correspondingly marked side of the transducer probe.

Figure 7A:
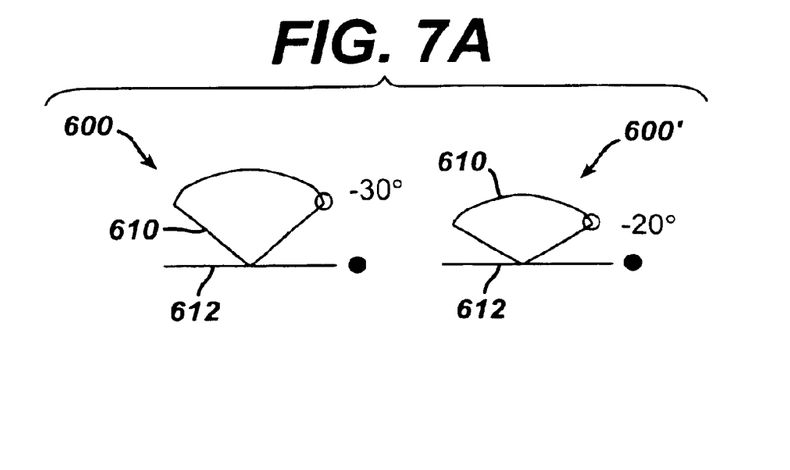
FIGS. 7A–7C illustrate the plane orientation icon of FIG. 6 for different image plane orientations.

The icon 600 of FIG. 6 indicates that the R image has been tilted to a plane of +30° in front of the plane of the L image. In FIG. 7A the left icon shows the icon 600 when the R image has been tilted to an orientation of −30° behind the plane of the L image. The icon 600' in FIG. 7A shows the icon when the R image has been tilted to an orientation which is −20° with respect to the L image. It can be seen that the aspect ratio of the sector part 610 of icon 600' has changes from that of icon 600 to represent the different tilt angle of the R image. Thus, as the image plane is tilted from an orientation of +30°, to a 0° orientation in which the L and R image planes are aligned and then through to a −30° orientation, the sector part 610 of the icon will start as shown in FIG. 6, collapse to a line which is aligned with line 612, and then expand back to the appearance shown at the left side of FIG. 7A.

Figure 7B:
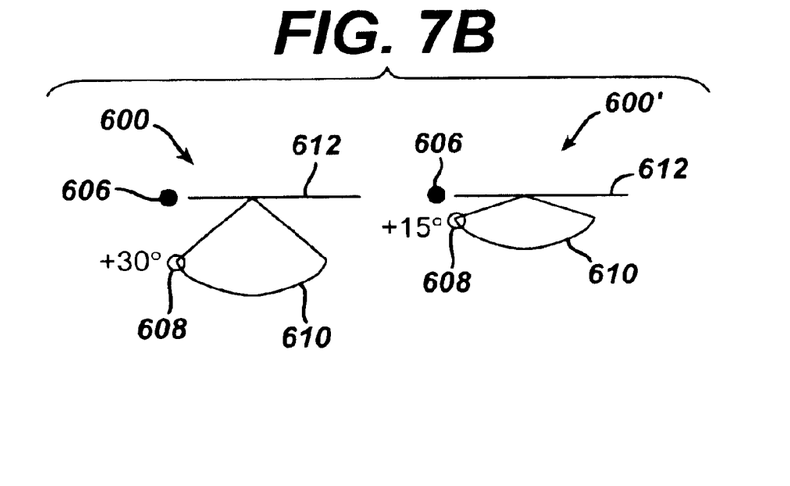
Figure 7C:
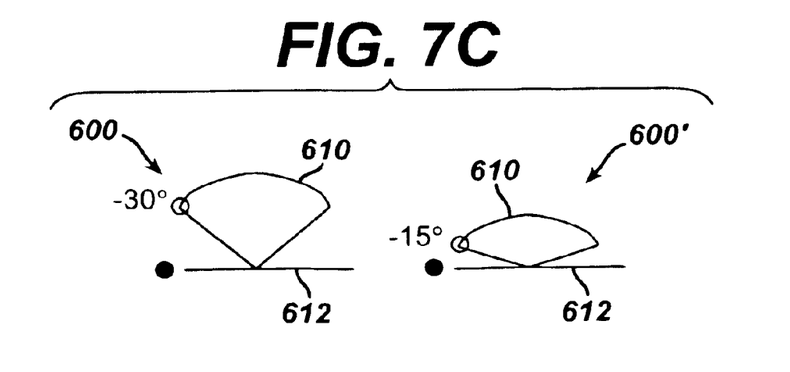

FIG. 7B shows +30° and +15° icons when the left-right orientation of both images has been inverted from that shown in FIGS. 6 and 7A. This is apparent from the shift of the left-right orientation dots 606 and 608 in FIG. 7B relative to the dots in FIGS. 6 and 7A. When these inverted sector images are tilted from the +30° and +15° tilt orientations depicted in FIG. 7B to −15° and −30° orientations the icons 600 and 600' will take on the appearances shown in FIG. 7C. The examples of FIGS. 7A–7C illustrate tilt orientation icons with numeric indications of the tilt orientation.

The lateral and elevation tilt features described above can be implemented in combination with the image rotation capability described in the parent patent [application Ser. No. 10/231,704]. For example, one image could be tilted relative to another in the elevation dimension, then rotated about its centerline to intersect a particular anatomy of interest. In a combined implementation the user is then able to both tilt and rotate one image plane relative to another, providing a versatile three dimensional diagnostic capability.

What is claimed is:

1. An ultrasonic diagnostic image display comprising:
   a first two dimensional image having an image plane orientation in relation to a transducer;
   a second two dimensional image having a plane orientation relative to the plane of the first two dimensional image; and
   a plane orientation icon, displayed on a display screen concurrently with the first and second images, which depicts the relative angular planar orientation of the first and second images, wherein the icon comprises a depiction of the changing aspect ratio of at least one of the image planes as seen from a common reference as the plane of one of the images is tilted relative to the other.

2. The ultrasonic diagnostic image display of claim 1, wherein the depicted aspect ratio of the icon further comprises the outline of an image.

3. The ultrasonic diagnostic image display of claim 2, wherein the image outline comprises the outline of a sector image.

4. The ultrasonic diagnostic image display of claim 1, wherein the common reference comprises the images as viewed from the transducer.

5. The ultrasonic diagnostic image display of claim 1, wherein the icon further comprises a left-right indicator of the orientation of the image with respect to a transducer probe.

6. The ultrasonic diagnostic image display of claim 1, wherein the image planes intersect each other at a plurality of planar orientations.

7. The ultrasonic diagnostic image display of claim 1, wherein the image planes intersect each other at one planar orientation.

8. The ultrasonic diagnostic image display of claim 7, wherein the image planes are co-planar when intersecting.

9. The ultrasonic diagnostic image display of claim 1, wherein the first and second two dimensional images comprise real-time ultrasonic images.

10. The ultrasonic diagnostic image display of claim 1, wherein the icon further comprises a numerical indication of the relative angular orientation of the image planes.

11. An ultrasonic diagnostic imaging system comprising:
    an ultrasound probe, including a left-right marker to identify a given side of an image, which acts to scan two different image planes in real time;
    a controller, coupled to the ultrasound probe, which controls the relative orientation of the image planes to be scanned by the probe;
    a user control, coupled to the controller, by which a user can vary the relative orientation of the image planes; and
    a display, coupled to the probe, which simultaneously displays images of the two image planes, at least one of which includes a left-right marker corresponding to the probe marker, and an icon indicating the relative orientation of the image planes which includes at least one left-right marker corresponding to the displayed image left-right marker.

12. The ultrasonic diagnostic imaging system of claim 11, wherein the indicator is responsive to variation of the user control to indicate the relative orientation of the image planes.

13. The ultrasonic diagnostic imaging system of claim 12, wherein each of the displayed images includes a left-right marker.

14. The ultrasonic diagnostic imaging system of claim 12, wherein the icon includes a left-right marker corresponding to each displayed image.

15. The ultrasonic diagnostic imaging system of claim 12, wherein the icon further comprises a projection of the aspect ratio of at least one of the images.

16. The ultrasonic diagnostic imaging system of claim 11, wherein the user control is variable to change the angle of inclination of one of the image planes in relation to the other image plane,
    wherein the icon indicates the angle of inclination and the left-right orientation of one of the image planes in relation to the other image plane.

* * * * *